United States Patent [19]

Whitaker

[11] Patent Number: 5,044,211
[45] Date of Patent: Sep. 3, 1991

[54] METHOD FOR DETERMINING THE EFFECTS OF OXYGEN PLASMA ON A SPECIMEN

[75] Inventor: Ann F. Whitaker, Huntsville, Ala.

[73] Assignee: The United States of America as represented by the Administrator of the National Aeronautics and Space Administration, Washington, D.C.

[21] Appl. No.: 386,174

[22] Filed: Jul. 28, 1989

[51] Int. Cl.$^5$ ........................ G01N 33/00; B05C 11/00
[52] U.S. Cl. ........................................ 73/866; 118/712; 118/724
[58] Field of Search ............... 73/864.83, 866, 865.6; 427/42; 315/111.21, 111.31, 111.41, 111.51, 111.61, 111.71; 118/723, 724, 712

[56] References Cited

U.S. PATENT DOCUMENTS

| | | | |
|---|---|---|---|
| 3,372,672 | 3/1968 | Wright et al. | 118/724 |
| 3,545,252 | 12/1970 | Springfield | 73/15 |
| 3,817,109 | 6/1974 | Audet | 73/432 SD |
| 4,241,165 | 12/1980 | Hughes et al. | 430/435 |
| 4,292,384 | 9/1981 | Straughan et al. | 156/643 |
| 4,312,835 | 1/1982 | Zoltan | 422/70 |
| 4,399,016 | 8/1983 | Tsukada et al. | 118/723 |
| 4,425,810 | 1/1984 | Simon | 73/863.11 |
| 4,440,108 | 4/1984 | Little et al. | 118/723 |
| 4,539,068 | 9/1985 | Takagi et al. | 118/723 |
| 4,588,641 | 5/1986 | Hague et al. | 427/41 |
| 4,627,287 | 12/1986 | Suga | 73/865.6 |
| 4,771,730 | 9/1988 | Tezuka | 118/724 |

FOREIGN PATENT DOCUMENTS 0094922  5/1987  Japan ..................... 118/723

*Primary Examiner*—William A. Cuchlinski, Jr.
*Assistant Examiner*—Alvin Wirthlin
*Attorney, Agent, or Firm*—Robert L. Broad, Jr.; Jerry L. Seemann

[57] ABSTRACT

A method for determining the effects of exposure of oxygen plasma on a specimen such as a thin film polymer or thin metals. The method includes providing an apparatus with a chamber having a holder supporting the polymer specimen in a plasma environment provided in the chamber. The chamber is regulated to a predetermined pressure and set temperature prior to the introduction of oxygen plasma therein. The specimen is then subjected to the plasma environment for a predetermined time during which time the temperature of the specimen is sensed and regulated to be maintained at the set temperature. Temperature sensing is accomplished by a probe which senses any changes in bulk sample temperature. Temperature regulation is provided by a thermoelectric module and by a coolant flow tube.

1 Claim, 2 Drawing Sheets

METHOD FOR DETERMINING THE EFFECTS OF OXYGEN PLASMA ON A SPECIMEN

ORIGIN OF THE INVENTION

The invention described herein was made by an employee of the United States Government and may be manufactured and used by or for the Government for governmental purposes without the payment of any royalties thereon or therefor.

TECHNICAL FIELD

This application is generally directed to thermal control in plasma conditions and more particularly to an apparatus and method for determining the effects of exposure of oxygen plasma on a film polymer or thin metals whose bulk is maintained at a predetermined temperature.

BACKGROUND OF THE INVENTION

The present invention concerns an apparatus and method for testing a specimen such as a film polymer or thin metals in a plasma environment whereby the effects of such environment may be ascertained. Testing is done in a chamber in an oxygen plasma environment. The test apparatus includes a platform for support of the specimen in the chamber and also includes temperature control devices and temperature sensing devices which are used to maintain a predetermined temperature on the couple during its exposure to the oxygen environment.

The use of test chambers for testing samples under various conditions are known in the art. A hyperbolic simulator, for example, is disclosed in U.S. Pat. No. 3,817,109 which is used to evaluate thickness change, stretch-flex change, thermal conductance and other material properties under simulated deep sea pressures down to 1,000 feet. The chamber includes a thermal conductance tester.

Another type of test chamber is disclosed in U.S. Pat. No. 3,545,252 which is directed to a flammability test chamber for testing materials in various environments. The material is tested to determine the flame propagation of the material. Tests are also performed to determine certain mechanical movements of the apparatus will create a spark in the material.

U.S. Pat. No. 4,425,810 discloses a chamber in which physical properties of a sample material is measured at controllable temperatures and pressure. The chamber includes a sample holder in combination with chamber heating and cooling means.

None of the above discussed patents disclose applicant's structure relating generally to the concept of a sample holder for use in a chamber having a plasma therein. Specifically, none of the patents are directed to, as is applicant's method and apparatus, to such a chamber having a closure member which serves as a support for a specimen supporting structure which also supports temperature sensing and temperature controlling means. Also, none of the patents are directed to a method and apparatus for exposing a specimen such as a film polymer or thin metal to an oxygen plasma environment while maintaining the specimen bulk at a predetermined temperature, whereby the nature of the specimen may be ascertained to determine the effects of the plasma environment.

It is an object of the present invention, therefore, to provide an apparatus and method for determining the effects of a plasma on a specimen supported in a chamber.

It is a further object of the present invention to provide such apparatus and method for making such determination on a film polymer whose bulk is maintained at a predetermined temperature.

It is yet another object of the present invention to provide the chamber with temperature sensing and temperature controlling devices.

It is yet another object of the present invention to provide an oxygen plasma environment in the chamber for testing the specimen therein.

DESCRIPTION OF THE PREFERRED EMBODIMENT

Figure 2:
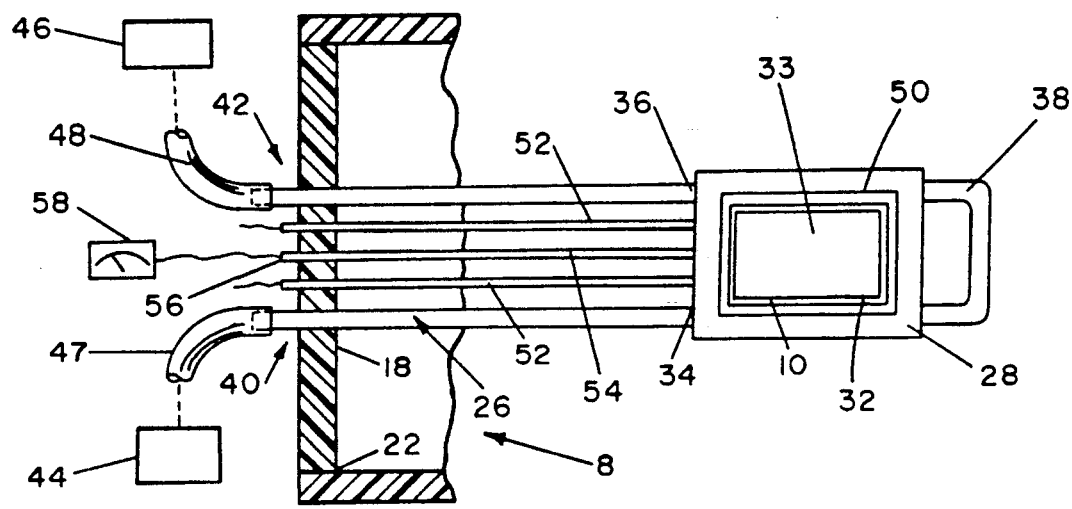
FIG. 2 is a plan view, partially broken away, of the test chamber of the present invention including the specimen and support structure therefor.
Figure 1:
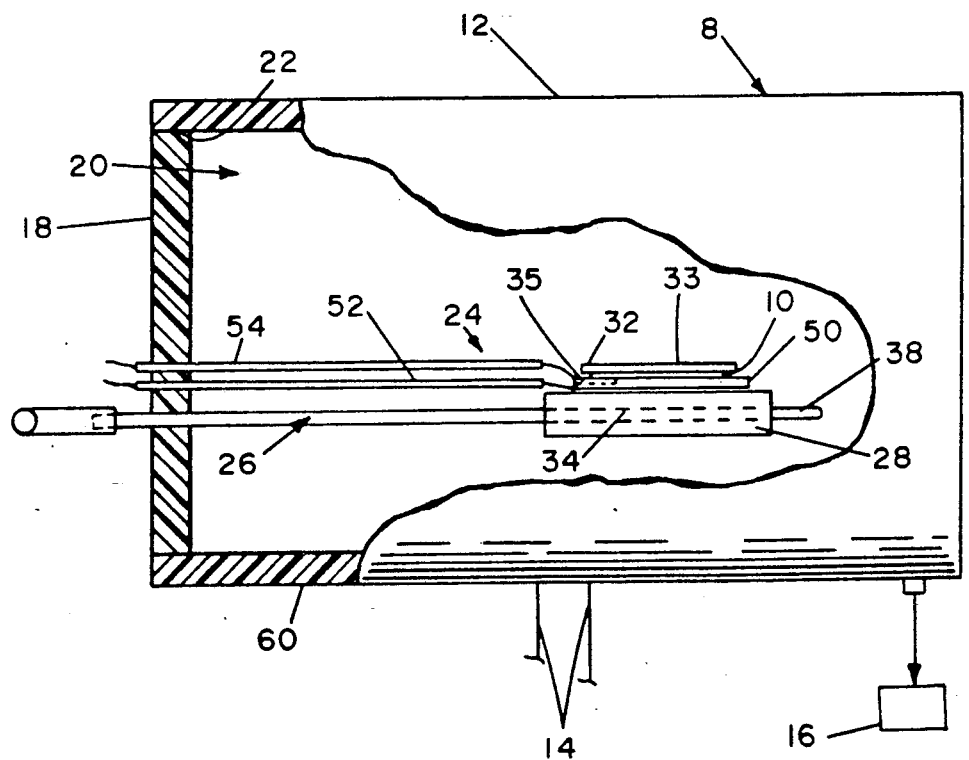
FIG. 1 is an elevational view, partially broken away, of the test apparatus of the present invention.
Figure 3:
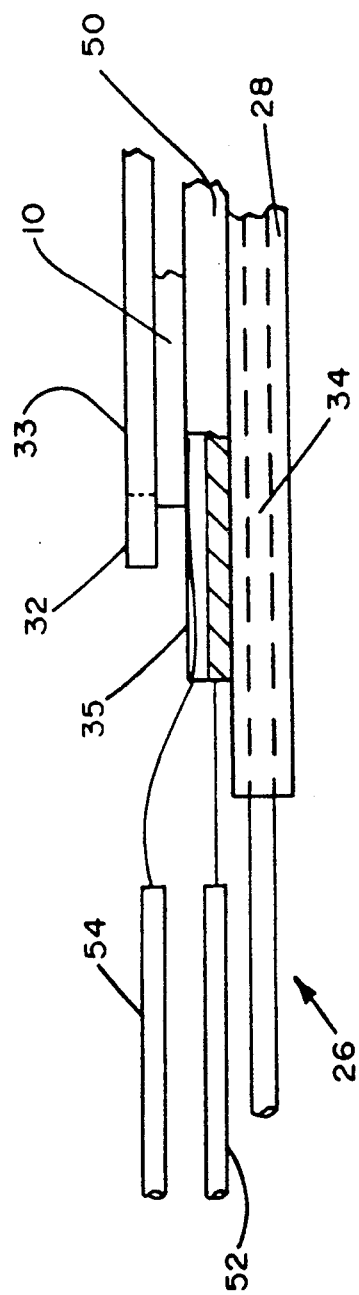
FIG. 3 is an enlarged partial plan view similar to FIG. 2 illustrating the relationship between the thermocouple probe and specimen of FIG. 2.

Referring now to the drawings, there is shown a reaction chamber 8 in which oxygen plasma is produced. The reaction chamber 8 carries a specimen 10, which may be a film polymer. The wall 12 of the chamber is typically made of Pyrex glass or the like. The chamber is connected to a source of RF energy 14 that provides up to 100 watts of continuous 13.56 MHz power into the chamber. The RF energy is used to dissociate molecular oxygen supplied into the chamber into oxygen plasma. A vacuum pump 16 is connected with the chamber. The reaction chamber is part of a small commercial reactor that with the exception of the external vacuum pump is a fully self-contained device sold under the trade name PLASMOD by the Tegal Corporation.

The test apparatus of the present invention includes a closure member 18 such as a plexiglass disc which serves as a support structure for the specimen 10 and for the thermal control apparatus used in the chamber. Closure member 18 is a hermetically sealed member which may be transparent so that conditions inside the chamber may be observed during the test procedure. The closure member serves as a door to the entrance opening 20 of the chamber and is adapted to fit within the entrance opening of the reaction chamber 8. A silicon seal 22 is used to seal the opening. Closure member 18 is silicon coated and supports the test apparatus 24 within the chamber.

The test apparatus 24 includes a cooling coil 26, typically copper, which is supported in closure member 18 and extends into chamber 8 to provide coolant to the test apparatus. A platform 28 is provided for support of specimen 10 and a glass plate protective cover 32 for the specimen. Cooling coil 26 includes portions 34 and 36 to which platform 28 is attached. The cooling coil preferably extends through platform 28 at portions 34 and 36 (FIG. 2) and may be imbedded therein. The cooling coil further includes a u-bend section 38 and a pair of end sections 40 and 42. End section 40 is connected to a thermal control bath 44 and end section 42 is connected to coolant receiving tank 46. Flexible hoses 47 and 48 may be provided at the end sections 40 and 42, if desired. The thermal control bath supplies water-glycol (23 C) to the platform to cool the test apparatus during testing.

Platform 28 is typically a small copper block which is approximately 4.4 centimeters long (along the axis of the cooling coil), 1.6 centimeters in depth and 3.8 centimeters in width, to minimize its effect on the plasma environment. Platform 28 serves as a base to support a thermoelectric module 50 including heating elements 52 and assists the module in maintaining a low test temperature for the test sample 10. Module 50 is available commercially as Melcor Model CP10127-05L, and has a surface area of approximately 9 cm$^2$ and thermally coupled to platform 28 by standard thermal transfer paste.

The material test specimen 10 is placed upon the thermoelectric module 50 and held in placed by the cover glass plate 32 having a specimen surface exposure area 33. The temperature of the sample is monitored by a thermocouple probe 54 which is spring loaded against a groove 35 in the thermoelectric module 50 and presses against the sample. The glass cover plate 32 holds the test material 10 firmly against the probe 54. The probe 54 signal wire 56 is insulated and extends back through the closure member to a meter 58. The cooling coil 26 and platform 28 is located adjacent a vacuum vent 60 to preclude the build up of a stagnant gas layer.

In operation, the sample 10 is placed on the module 50 and the test apparatus is inserted into the reaction chamber with the disc closure member sealing the chamber. The reaction chamber pressure is reduced and then backfilled by gaseous oxygen of 99.9 percent purity to a stable pressure in the range of 600 to 900 millitorr. The sample 10 is heated or cooled by the thermoelectric device (assisted by the cooled platform 28) and allowed to stabilize at a set temperature for approximately fifteen minutes. After the system pressure and the material temperature have stabilized, the power is applied to produced the oxygen plasma. Visible glow of oxygen is then observed. Any changes in bulk sample temperature detected by the thermocouple probe are quickly adjusted to maintain the initial bulk material temperature by the thermoelectric module 50. The base temperature of the sample 10 has been found to be essentially at the temperature of its surface, that is within 3 degrees of the base temperature.

In previous tests, material specimens were exposed nominally for thirty minutes without interruptions at a specified temperature with accumulation of data. The PLASMOD is operated at a low wattage so that the ambient plasma temperature is near the lowest sample test temperature. This allows for more accurate data and closer thermal control of the test sample. Nominal test temperatures were 10, 45, 75 degrees Celius. No lower temperature was chosen as a test temperature because of the concern for possible gaseous molecular condensation on the material sample. The upper temperature bound was chosen because the thermoelectric module 50 could become inefficient after lengthy operation at 80 to 85 degrees centigrade and the upper use temperature of plasma exposure was approached. Plasma exposures up to thirty minutes were necessary for such materials as polytetrafluoroethylene because of its low mass loss rate. Residual gas analyses may be made of the gases in the reaction chamber to provide additional insight into the fracture of the polymer under atomic oxygen attack if desired.

I claim:

1. A method for testing a temperature controlled specimen in a plasma environment, whereby the effects of said plasma environment on said specimen may be ascertained comprising:

placing the specimen on a holder and positioning said specimen holder in a chamber of a test apparatus disposed for generating said plasma environment therein;

reducing the chamber pressure and back-filling said chamber with a gas to a stable pressure;

temperature controlling said specimen and allowing said specimen to stabilize at a set temperature at said stable pressure for a predetermined time;

generating said plasma environment by applying a source of electric power for ionization of said gas to produce the desired plasma environment after said specimen has stabilized at said set temperature;

continuously sensing the temperature of said specimen during exposure thereof to said plasma environment to sense any temperature variations of said specimen during said exposure as said temperature variations occur in said specimen;

adjusting the temperature of said specimen to said set temperature responsive to said temperature variations;

ascertaining the nature of said specimen after exposure thereof to said plasma environment to determine if any fractures have occurred as a result of said exposure.

* * * * *